United States Patent [19]

Cowdery

[11] 3,971,388
[45] July 27, 1976

[54] TITANIUM COVERED CARDIAC PACEMAKER WITH ELASTOMER COATING AND METHOD OF APPLYING SAME

[75] Inventor: David J. Cowdery, Elanora, Australia

[73] Assignee: Telectronics Pty. Limited, Australia

[22] Filed: Nov. 29, 1974

[21] Appl. No.: 528,091

[52] U.S. Cl. .......................... 128/419 P; 427/340
[51] Int. Cl.² .................................. A61N 1/36
[58] Field of Search ............. 128/419 P; 117/119, 117/132 BS, 135.1, 161 ZA; 427/2

[56] References Cited
UNITED STATES PATENTS

| | | | |
|---|---|---|---|
| 2,999,852 | 9/1961 | Renfrew et al. | 117/132 BS |
| 3,101,277 | 8/1963 | Eder et al. | 117/132 BS |
| 3,169,079 | 2/1965 | Ferington et al. | 117/119 |
| 3,195,540 | 7/1965 | Waller | 128/419 P |
| 3,455,732 | 7/1969 | Hathaway, Jr. | 117/132 BS |
| 3,649,367 | 3/1972 | Puroy | 128/419 P |
| 3,754,967 | 8/1973 | Greenlee | 117/132 BS |
| 3,866,616 | 2/1975 | Purdy et al. | 128/419 P |

*Primary Examiner*—William E. Kamm
*Attorney, Agent, or Firm*—Flehr, Hohbach, Test, Albritton & Herbert

[57] ABSTRACT

An implantable cardiac pacemaker which is enclosed in a titanium or titanium alloy housing with at least a portion of the housing coated with a silicone elastomer which both electrically and physiologically isolates the metal surface from the body while at the same time permitting the body tissue to act on the elastomer itself to provide a form of adhesion thereby to assist in stabilizing the pacemaker position within the body.

8 Claims, 2 Drawing Figures

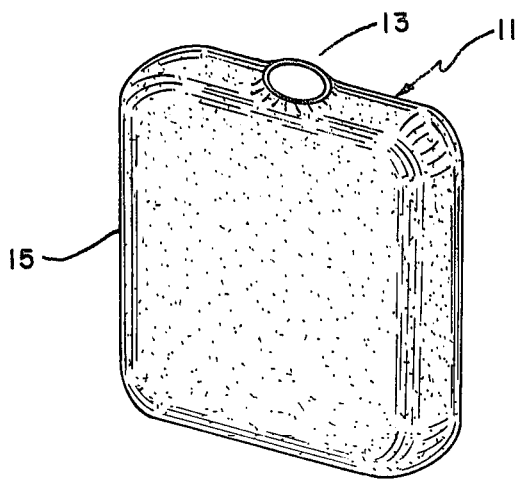
FIG.—1
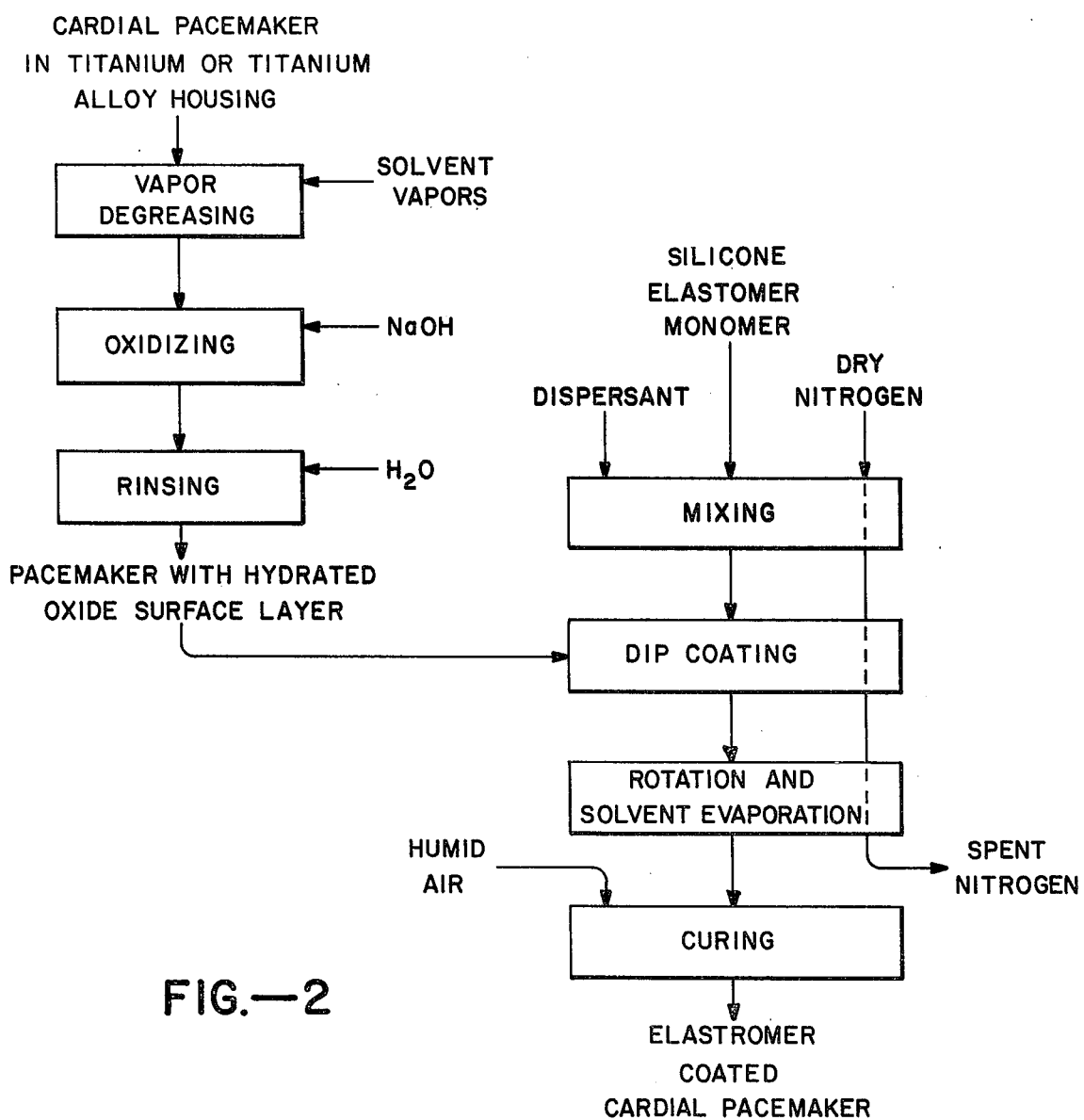
FIG.—2

TITANIUM COVERED CARDIAC PACEMAKER WITH ELASTOMER COATING AND METHOD OF APPLYING SAME

BACKGROUND OF THE INVENTION

The use of titanium or titanium alloy covering cardiac pacemakers is well known. In some instances such pacemakers are hermetically sealed in the titanium or titanium alloy housing while in others the pacemaker is encapsulated in a polymer and the titanium housing is provided primarily for shielding to reduce the effect of interference on the action of the pacemaker. In some instances the titanium or titanium alloy housing forms a part of the stimulating circuit of the pacemaker and requires intimate contact with the body of the patient. In other instances no such contact is required between the titanium housing and the body of the patient, the entire contact with the body tissue being by means of electrodes external of the pacemaker.

Whenever a titanium or a titanium alloy is exposed to the body fluids there is a possibility that a galvanic cell and galvanic corrosion may occur in conjunction with any other implanted metals in the body. Moreover, the release of titanium into the tissues surrounding the implant may at times occur.

In those instances where the titanium housing forms a part of the stimulating circuit there may be problems of skeletal muscle stimulation whenever the pacemaker is placed close to contractal tissue.

SUMMARY OF THE INVENTION AND OBJECTS

The invention relates to cardiac pacemakers embodying a covering of titanium or any of its alloys and particularly such a pacemaker wherein an elastomer covering is applied over the titanium to provide electrical and physiological insulation. It is a specific object of the invention to obviate the disadvantages of direct contact of titanium or titanium alloy with the body fluids and in those instances where the housing forms a part of the stimulating circuit, to limit the contact of the titanium housing by coating a major portion of the housing itself. The titanium or titanium alloy is thus exposed to the body only at a selected region and that region may be optimally oriented within the implant site so as to minimize local skeletal muscle stimulation.

It is a further object of the invention to provide a method for coating the surface of titanium or titanium alloy covered pacemakers with an elastomer of medical quality.

BRIEF DESCRIPTION OF THE DRAWING

FIG. 1 is a perspective view of a cardiac pacemaker fully coated with an elastomer in accordance with the invention; and FIG. 2 is a flow chart showing the method in which the pacemaker is coated with elastomer.

DETAILED DESCRIPTION OF THE PREFERRED EMBODIMENT

Referring specifically to FIG. 1, there is shown a pacemaker 11 in accordance with the invention having an electrode connection 13 and a body 15. The body 15 is in the form of a housing which may be of titanium or of some titanium alloy and is covered with a silicone elastomer. When the pacemaker is subsequently placed within the body cavity a silicone elastomer electrically insulates the titanium surface of the pacemaker from the surrounding conductive fluid in the body. Moreover, once implanted the body tissue acts on the elastomer rather than on the titanium.

Referring to FIG. 2, there is shown a flow chart of the various steps employed in coating a pacemaker in accordance with the invention. The procedure is started with a cardiac pacemaker circuit in a housing formed of titanium or some titanium alloy. Ordinarily the housing hermetically seals the circuit within but may serve merely as a shielding shell for an enclosed polymer encapsulated device. In any event, the titanium housing is first subjected to vapor degreasing in an atmosphere of toluene, trichlorethylene and Freon, a trademark of E. I. DuPont de Nemours for a halogenated hydrocarbon used as a propellant. After degreasing the pacemaker is then soaked in a 0.01 molar solution of sodium hydroxide which forms a hydrated oxide surface layer on the titanium or titanium alloy. After such oxidation the pacemaker is rinsed by soaking it in distilled water and is then in a state ready to receive the elastomer.

In preparation of the elastomer, the elastomer itself, preferably medical Silastic A, a trademark of Dow Chemical Company for a heat stable silicon elastomer, is mixed in solvent dispersant. The dispersant should be either benezene or one of the homologues of benezene, preferably either methyl benezene or dimethyl benezene. When either methyl benezene or dimethyl benezene are employed it has been found that a satisfactory concentration has been four ounces (113 grams) of medical Silastic A to about 7.1 ounces (210 milliliters) of the dispersant.

The dispersion, as well as the following steps of coating and solvent evaporation are all performed in a dry inert atmosphere such as of argon or nitrogen which prevent elastomer reaction. The atmosphere should be dry and a dew point of approximately −60° C. is recommended.

After the elastomer has been dispersed the pacemaker is then dip coated in the solution. After dip coating the pacemaker is removed and rotated about its own axis at a rate of about 12 revolutions per minute still within the same dry and inert atmosphere. A continuous flow, at about 1 foot per second, of dry inert gas at 35° C. is maintained past the drying pacemaker until the bulk of the dispersant solvent has evaporated. Typically this evaporation takes about 2½ hours with the coating solution specified.

After the solvent has been evaporated the pacemaker, coated with the monomer, free of dispersant solution is continued to be rotated but now on an atmosphere of flowing air at about 35° C. and at about 80% to 100% relative humidity, for about 100 hours, which cures the elastomer. After such curing the pacemaker is completed.

I claim:

1. A method of applying a flexible silicone elastomer to an implantable heart pacemaker enclosed within a housing formed of a material from the group including titanium and titanium alloys comprising dispersing a silicone elastomer in a solvent from the group including benezene, methyl benezene and dimethyl benezene, dipping the heart pacemaker in the dispersed elastomer, evaporating the solvent from the elastomer and curing the elastomer coating in a humid environment.

2. The method of claim 1 wherein the steps of dispersing, dipping and evaporating are all accomplished in an inert dry atmosphere whereby elastomer reaction is prevented.

3. The method of claim 2 wherein said atmosphere is argon at 35° C. and having a dew point of approximately −60° C.

4. The method of claim 2 wherein said atmosphere is nitrogen at 35° C. and having a dew point of approximately −60° C.

5. The method of claim 2 wherein said step of evaporating comprises blowing a continuous flow of inert gas at about one foot per second, past the pacemaker until the dispersant solvent has evaporated.

6. The method of claim 5 wherein said inert gas is at about 35° C. and the flow of gas is continued for about 2½ hours.

7. The method of claim 1, together with the step of creating a hydrated oxide surface layer on said housing prior to dipping the pacemaker whereby optimum adhesion is produced.

8. The method as set forth in claim 7 wherein the hydrated oxide surface layer is created by soaking the housing in a 0.01 molar solution of sodium hydroxide and rinsing the hydroxide soaked pacemaker in distilled water.

* * * * *